United States Patent
Lin et al.

(10) Patent No.: US 10,034,648 B2
(45) Date of Patent: Jul. 31, 2018

(54) SYSTEM AND METHOD FOR MOTION ARTIFACTS REDUCTION

(71) Applicant: Carestream Health, Inc., Rochester, NY (US)

(72) Inventors: Yuan Lin, Rochester, NY (US); William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 38 days.

(21) Appl. No.: 15/165,159

(22) Filed: May 26, 2016

(65) Prior Publication Data
US 2017/0196529 A1 Jul. 13, 2017

Related U.S. Application Data

(60) Provisional application No. 62/277,994, filed on Jan. 13, 2016.

(51) Int. Cl.
*A61B 6/00* (2006.01)
*A61B 6/03* (2006.01)
*A61B 6/14* (2006.01)

(52) U.S. Cl.
CPC .............. *A61B 6/527* (2013.01); *A61B 6/032* (2013.01); *A61B 6/14* (2013.01); *A61B 6/4014* (2013.01); *A61B 6/4085* (2013.01); *A61B 6/461* (2013.01); *A61B 6/5211* (2013.01); *A61B 6/54* (2013.01)

(58) Field of Classification Search
CPC ......... A61B 6/032; A61B 6/14; A61B 6/4014; A61B 6/4085; A61B 6/461; A61B 6/5211; A61B 6/527; A61B 6/54
See application file for complete search history.

(56) References Cited

U.S. PATENT DOCUMENTS

| | | | |
|---|---|---|---|
| 4,994,965 A | 2/1991 | Crawford et al. | |
| 5,251,128 A | 10/1993 | Crawford | |
| 2008/0095302 A1 | 4/2008 | Ruhrnschopf et al. | |
| 2009/0149741 A1 | 6/2009 | Heigl | |
| 2010/0208274 A1* | 8/2010 | Kindlein | A61B 6/08 356/603 |
| 2011/0033024 A1* | 2/2011 | Dafni | A61B 6/032 378/8 |

FOREIGN PATENT DOCUMENTS

WO 2016/003957 1/2016

OTHER PUBLICATIONS

Jason Geng, "Structured-light 3D Surface Imaging: A Tutorial, Advances in Optics and Photonics," 2011, 3(2), pp. 128-160.
(Continued)

*Primary Examiner* — Siamak Harandi

(57) ABSTRACT

A system for reconstructing a 3D volume has a surface acquisition system with a light source and an image sensor for characterizing the surface contour of a patient and an X-ray imaging system for acquiring X-ray projection data of the patient from a number of angular positions. A controller is programmed with instructions to synchronize the 3D surface contour characterization from the surface acquisition system with the acquired X-ray projection data. A processor executes a motion reduction method that uses the acquired X-ray projection data and the generated 3D surface contour characterization to reconstruct a 3D volume.

20 Claims, 14 Drawing Sheets

(56) References Cited

OTHER PUBLICATIONS

F. Edward Boas and Dominik Fleischmann, "CT Artifacts: Causes and Reduction Techniques," Imaging in Medicine 4.2, 2012, pp. 229-240.
Jiang Hsieh, "Computed Tomography: Principles, Design, Artifacts, and Recent Advances," Bellingham, WA, SPIE, 2009, Chapter 7, 22 pages.

* cited by examiner

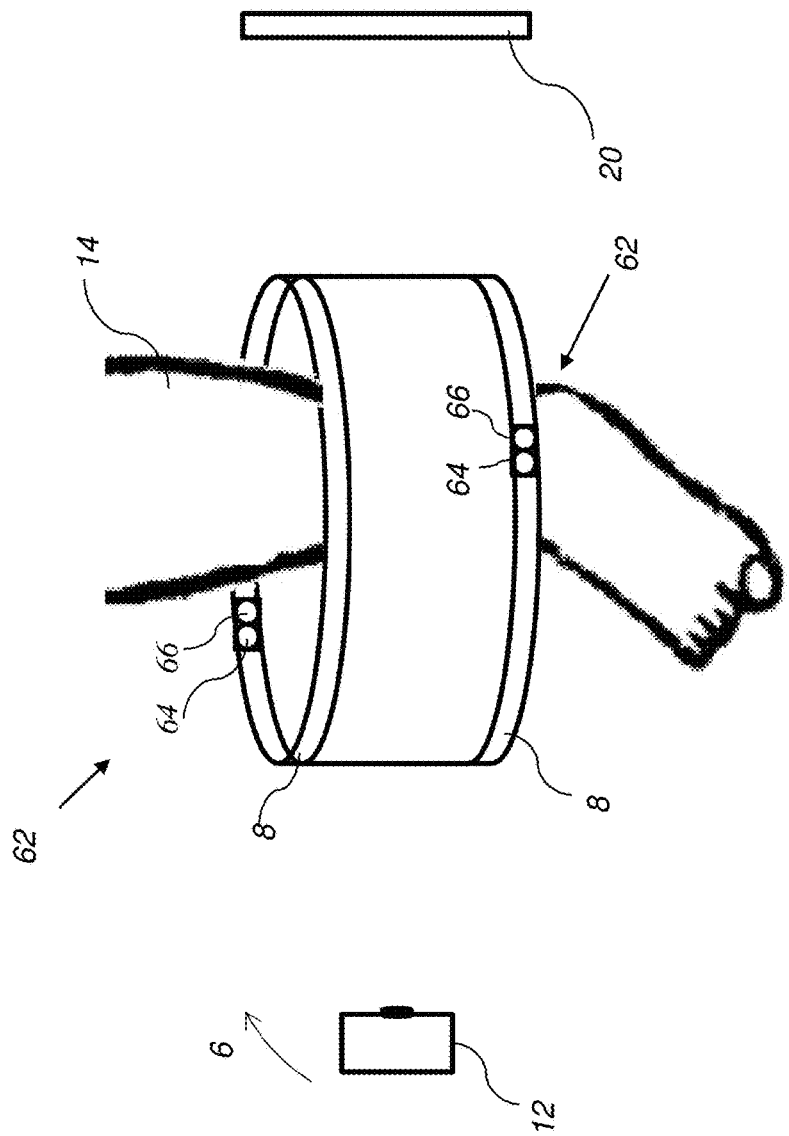

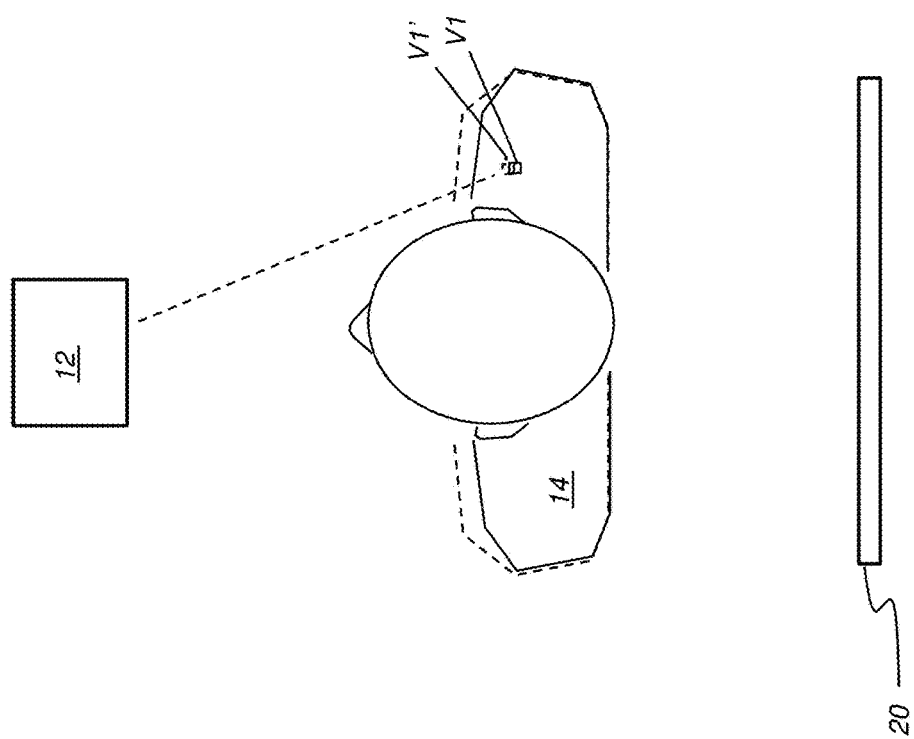

SYSTEM AND METHOD FOR MOTION ARTIFACTS REDUCTION

CROSS REFERENCE TO RELATED APPLICATIONS

This application claims the benefit of U.S. Provisional application U.S. Ser. No. 62/277,994, provisionally filed on Jan. 13, 2016, entitled "SYSTEM AND METHOD FOR MOTION ARTIFACTS REDUCTION", in the name of Yuan Lin et al, incorporated herein in its entirety.

TECHNICAL FIELD

The present invention relates, in general, to the field of 3-D medical imaging and more particularly, to a system and method to reduce artifacts in the reconstructed images caused by patient motion during image acquisition.

BACKGROUND

A number of techniques have been proposed for improving X-ray imaging results by improving the accuracy of the X-ray imaging system. System equipment improvements, however, address only part of the problem. It is estimated, for example, that a significant contribution to measurement inaccuracy is not due to problems with the X-ray imaging system, but is rather a result of patient motion. Because of patient movement during image acquisition, projections acquired at different time increments may not represent the attenuation line integrals of the same object. The inconsistent projections that result can lead to image artifacts, which are termed motion artifacts in the literature.

Patient motion is commonly observed during X-ray exams. For example, in conventional computed tomography (CT) exams, the normal respiration cycle can cause motion. In dental cone-beam CT (CBCT) and chest tomosynthesis, images exhibit a relatively higher number of motion artifacts, as patients are usually in sitting or standing positions and the acquisition time for projection images is longer. Repeat scans are sometimes inevitable when patient motion is excessive. X-ray imaging with low-cost CT is a challenge as a patient must sit still or stand motionless on a rotational support and be scanned by a stationary X-ray source and a stationary detector.

Problems with patient motion can be barriers to broader acceptance and use of volume imaging systems. Because of the significant patient motion, for example, the utility of low-cost CT has been limited in many developing countries.

Thus, there is a need for methods that compensate for patient motion and help to reduce the occurrence of motion-related artifacts.

The disclosure above is merely provided for general background information and is not intended to be used as an aid in determining the scope of the claimed subject matter. The invention is defined by the claims.

SUMMARY

Certain embodiments described herein address the need for methods that compensate for patient motion and help to reduce the occurrence of motion-related artifacts in diagnostic imaging.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a system for reconstructing a 3D volume comprising: a surface acquisition system comprising a light source and an image sensor for generating 3D surface models of a patient; an X-ray imaging system for acquiring X-ray projection data of the patient from a plurality of angular positions; a controller programmed with instructions to synchronize 3D surface models from the surface acquisition system with the acquired X-ray projection data; and a processor that executes a motion reduction method that uses the acquired X-ray projection data and the generated 3D surface models to reconstruct a 3D volume.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 3F is a schematic view diagram that shows an extremity X-ray imaging apparatus with multiple surface acquisition devices that can move independently on rails during projection data acquisition.

FIG. 4 is a schematic diagram that shows change in voxel position due to patient movement.

DETAILED DESCRIPTION OF THE EMBODIMENTS

Figure 1:
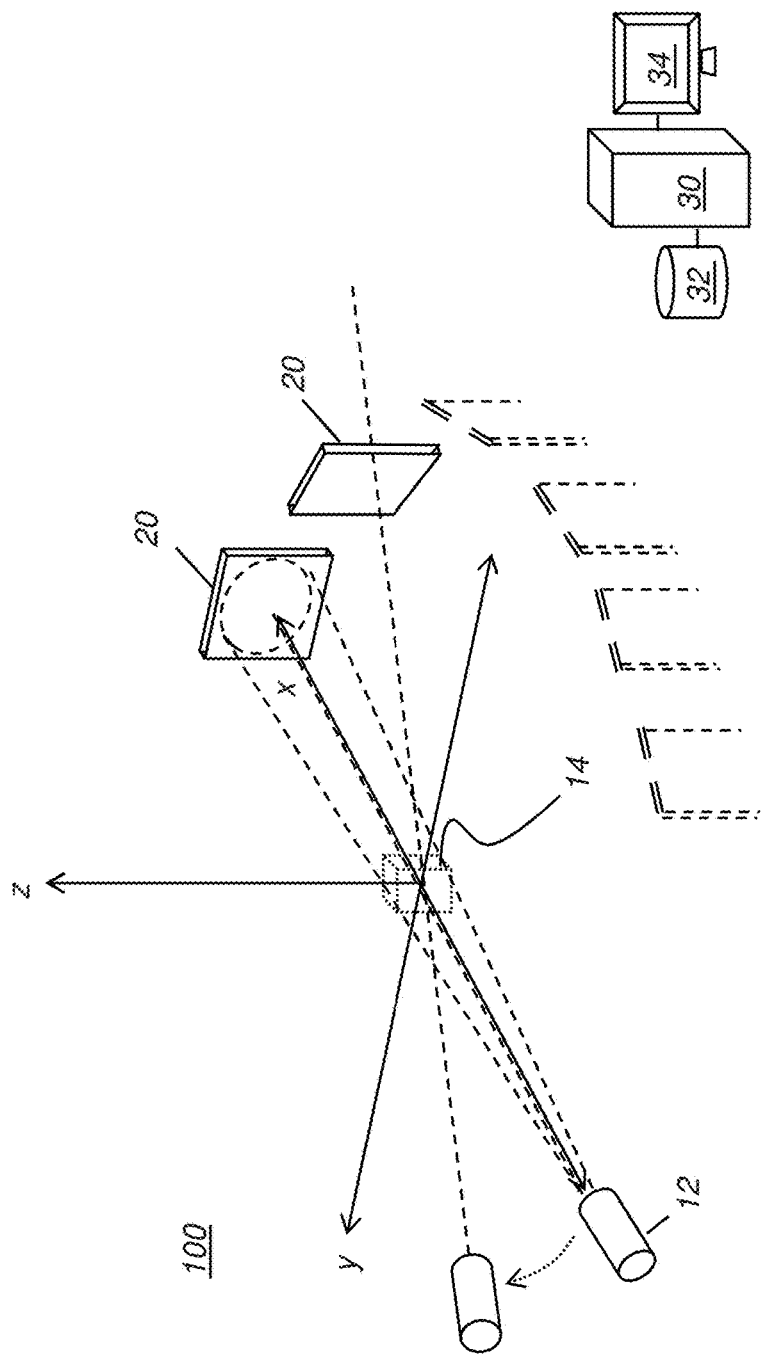
FIG. 1 is a schematic view that shows components of a CBCT image capture and reconstruction system.

The following is a detailed description of the embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", for example.

In the context of the present disclosure, "volume image content" describes the reconstructed image data for an imaged subject, generally stored as a set of voxels. Image display utilities use the volume image content in order to display features within the volume, selecting specific voxels that represent the volume content for a particular slice or view of the imaged subject. Thus, volume image content is the body of resource information that is obtained from a CT, CBCT, MDCT, tomosynthesis, or other volume imaging reconstruction process and that can be used to generate depth visualizations of the imaged subject.

Examples given herein that may relate to particular anatomy or imaging modality are considered to be illustrative and non-limiting. Embodiments of the present disclosure can be applied for both 2D imaging modalities (such as, for example: radiography, fluoroscopy, or mammography), and 3D imaging modalities (such as, for example: CT, MDCT, CBCT, tomosynthesis, dual energy CT, or spectral CT).

In the context of the present disclosure, the term "volume image" is synonymous with the terms "3 dimensional image" or "3D image".

In the context of the present disclosure, a radiographic projection image, more simply termed a "projection image" or "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

In the context of the present disclosure, the equivalent terms "surface contour imaging", "surface contour characterization", or "3D surface imaging" relate to forming a model or image of the surface contour of a subject, characterizing the overall volume of the subject according to its outer surface shape, but not defining internal features beneath the skin surface. Surface contour imaging techniques include methods that use reflectance images, such as those obtained from reflectance of visible light or near-infrared light from the surface, as described in more detail subsequently. Surface contour imaging algorithms can be used to form a surface model, reconstructed from structured light imaging or from other types of imaging input, typically from reflectance 2D images.

In order to more fully understand the methods of the present disclosure and the problems addressed, it is instructive to review principles and terminology used for 3-D volume image capture and reconstruction. Referring to the perspective view of FIG. 1, there is shown, in schematic form and using enlarged distances for clarity of description, the activity of a conventional CBCT imaging apparatus 100 for obtaining, from a sequence of 2D radiographic projection images, 2D projection data that are used to reconstruct a 3D volume image of an object or volume of interest, also termed a subject 14 in the context of the present disclosure. Cone-beam radiation source 12 directs a cone of radiation toward subject 14, such as a patient or other subject. For a 3D or volume imaging system, the field of view (FOV) of the imaging apparatus is the subject volume that is defined by the portion of the radiation cone or field that impinges on a detector for each projection image. A sequence of projection images of the field of view is obtained in rapid succession at varying angles about the subject, such as one image at each 1-degree angle increment in a 200-degree orbit. X-ray digital radiation (DR) detector 20 is moved to different imaging positions about subject 14 in concert with corresponding movement of radiation source 12. FIG. 1 shows a representative sampling of DR detector 20 positions to illustrate schematically how projection data are obtained relative to the position of subject 14. Once the needed 2D projection images are captured in this sequence, a suitable imaging algorithm, such as filtered back projection (FBP) or other conventional technique, is used for reconstructing the 3D volume image. Image acquisition and program execution are performed by a computer 30 or by a networked group of computers 30 that are in image data communication with DR detector 20. Image processing and storage is performed using a computer-accessible memory 32. The 3D volume image can be presented on a display 34.

Surface Contour Acquisition

In order to track patient motion during projection image acquisition, the imaging apparatus needs sufficient data for detecting surface displacement. To obtain this surface modeling information, an embodiment of the present disclosure can employ surface contour acquisition, such as contour acquisition using structured light imaging.

Figure 2:
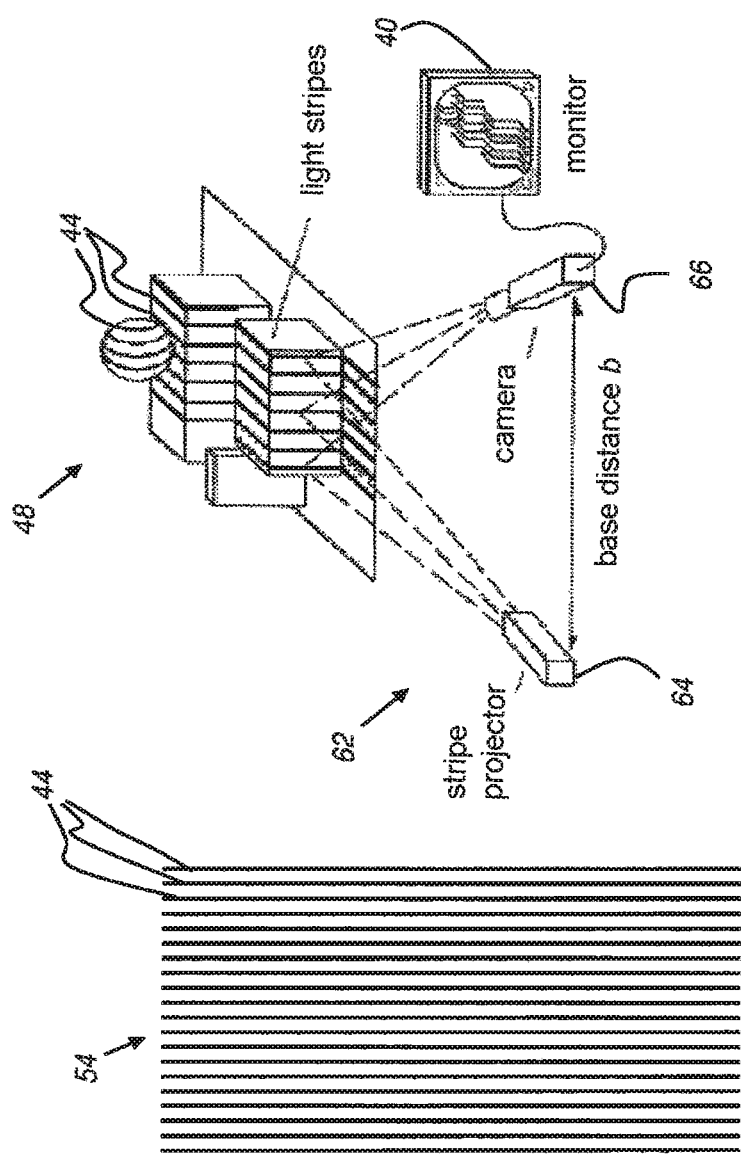
FIG. 2 is a schematic diagram that shows principles and components used for surface contour acquisition using structured light.

FIG. 2 shows surface contour acquisition principles, in schematic form. Surface contour acquisition can be provided from a scanner 62 having a projector 64 that directs a pattern 54 (for example, a pattern of lines 44) or other features individually from a laser source at different orbital angles toward a surface 48, represented by multiple geometric shapes. The combined line images, recorded by a camera or other type of image sensor 66 from different angles but registered to geometric coordinates of the imaging system, provide structured light pattern information. Triangulation principles, using known distances such as base distance b between camera 66 and projector 64, are employed in order to interpret the projected light pattern and compute contour information for patient anatomy or other surface from the detected line deviation. Lines 44, or other projected pattern, can be visible light or light of infrared wavelengths not visible to the patient and to the viewer, but visible to the appropriate imaging sensors. An optional monitor 40 shows the acquired surface contour as reconstructed by computer processor logic using one or more surface contour reconstruction algorithms.

Other methods for obtaining the surface contour can alternately be used. Alternate methods include stereovision technique, structure from motion, and time-of-flight techniques, for example. The surface contour can be expressed as a mesh, using techniques familiar to those skilled in the contour imaging arts.

The surface acquisition system can use a structured light imaging technique, using one or more light sources and one or more light sensors as shown in FIG. 2. The surface acquisition system projects, onto the patient, a known pattern of a light grid using the light sources. The deformed light pattern can be monitored by light sensors and analyzed by a host processor or computer to reconstruct a 3D surface model of the object. An exemplary structured light technique is described in Jason Geng, Structured-light 3D surface imaging: a tutorial. Advances in Optics and Photonics, 2011. 3(2): p. 128-160, incorporated herein in its entirety by reference. Advantageously, 3D surface contour generation using structured light requires very little time for image acquisition and processing.

Both surface contour characterization and volume image content are used for motion compensation and correction of the present disclosure. This image content can be acquired from previously stored data that can be from the same imaging apparatus or from different apparatus. However, there can be significant advantages in obtaining the surface contour characterization and volume image content from the same apparatus, particularly for simplifying the registration task.

Exemplary Apparatus

Figure 3A:
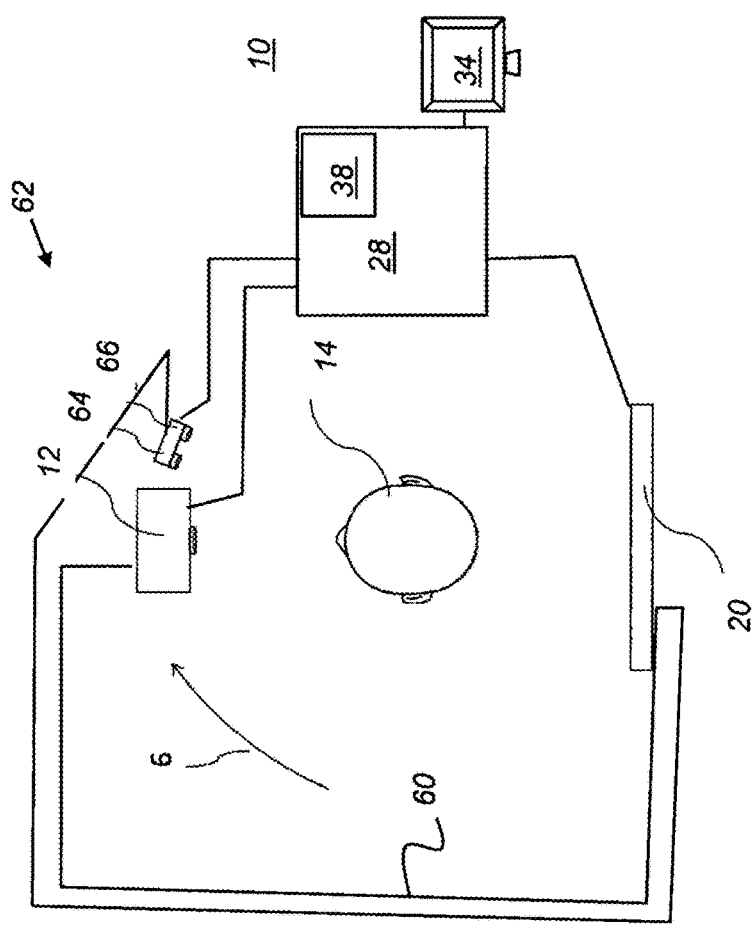
FIG. 3A is a top view schematic diagram of a CBCT imaging apparatus using a rotational gantry for simultaneously acquiring surface contour data using a surface contour acquisition device during projection data acquisition with an X-ray tube and detector.

FIGS. 3A-3E and 3G show top view component configurations for a number of different imaging apparatus 10 configurations for acquiring both surface contour and reconstructed volume image data according to embodiments of the present disclosure. FIG. 3A shows an arrangement using a rotational gantry 60 that provides a transport apparatus for orbiting x-ray source 12 and detector 20 about subject 14, along with light scanner 62 for surface contour characterization having light pattern projector 64 and camera or sensor 66. A rotation direction 6 is shown. A control logic processor 28 is in signal communication with x-ray source 12, detector 20, and scanner 62 components for surface characterization. Control logic processor 28 shown in FIGS. 3A-3E can include a controller 38 that coordinates image acquisition between scanner 62 and the radiography apparatus in order to identify and characterize patient motion for control of image acquisition and to support subsequent processing of the x-ray projection image data. Control logic processor 28 can also include the logic for projection image processing and for volume CT image reconstruction as well as surface contour characterization, or may provide connection with one or more additional computers or processors that perform the volume or surface contour reconstruction function and display of volume imaging results, such as on display 34. The FIG. 3A configuration may serve, for example, for a dental imaging device using CBCT combined with structured light imaging.

Figure 3B:
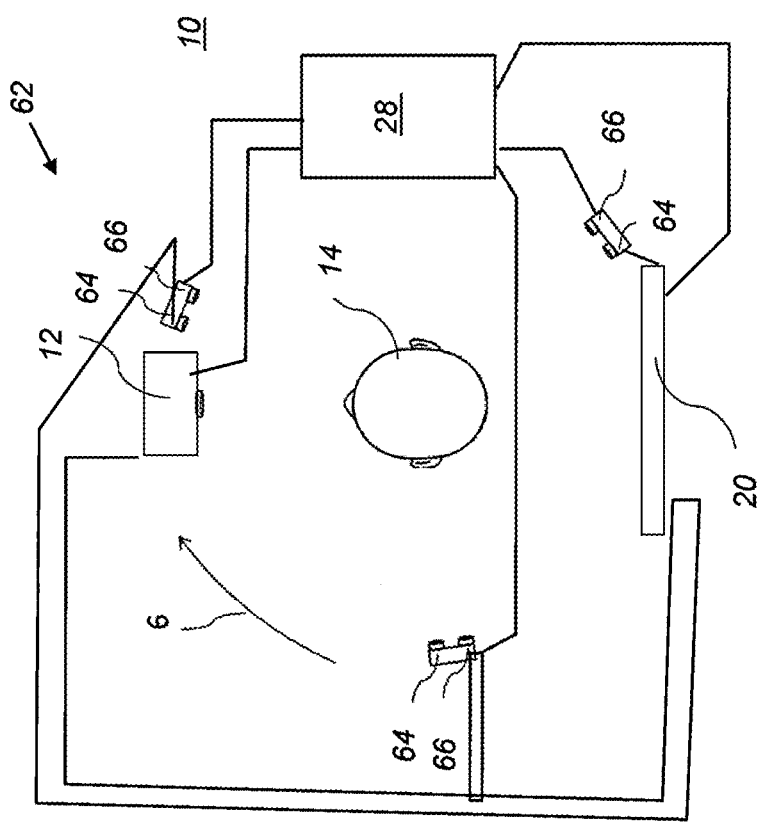
FIG. 3B is a top view schematic diagram of a CBCT imaging apparatus using a rotational gantry for simultaneously acquiring surface contour data using multiple surface contour acquisition devices during projection data acquisition with an X-ray tube and detector.

FIG. 3B shows an arrangement with gantry 60 having x-ray source 12 and detector 20 and a number of pattern projectors 64 and cameras or sensors 66 that provide light scanner 62 for surface characterization.

Figure 3C:
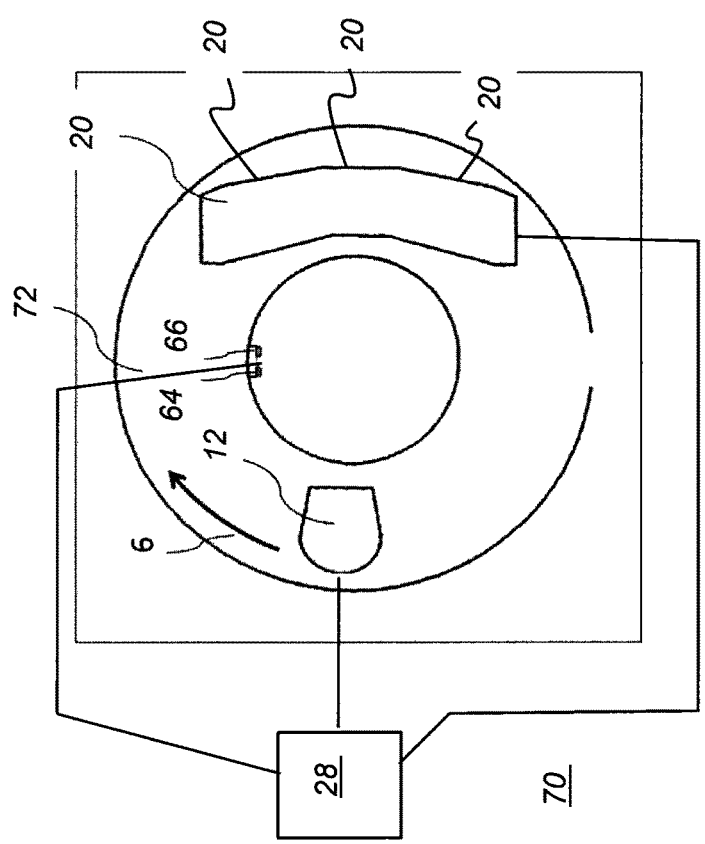
FIG. 3C is a top view schematic diagram of an imaging apparatus for a multi-detector CT (MDCT) system using one surface contour acquisition device affixed to the bore of the MDCT system during projection data acquisition.

FIG. 3C is a schematic diagram showing an MDCT (Multiple-Detector Computed Tomography) apparatus 70 that provides a single x-ray source 12 and a bank of multiple x-ray detectors 20 within a stationary bore 72. A projector 64 and camera 66 are also provided for contour imaging.

Figure 3D:
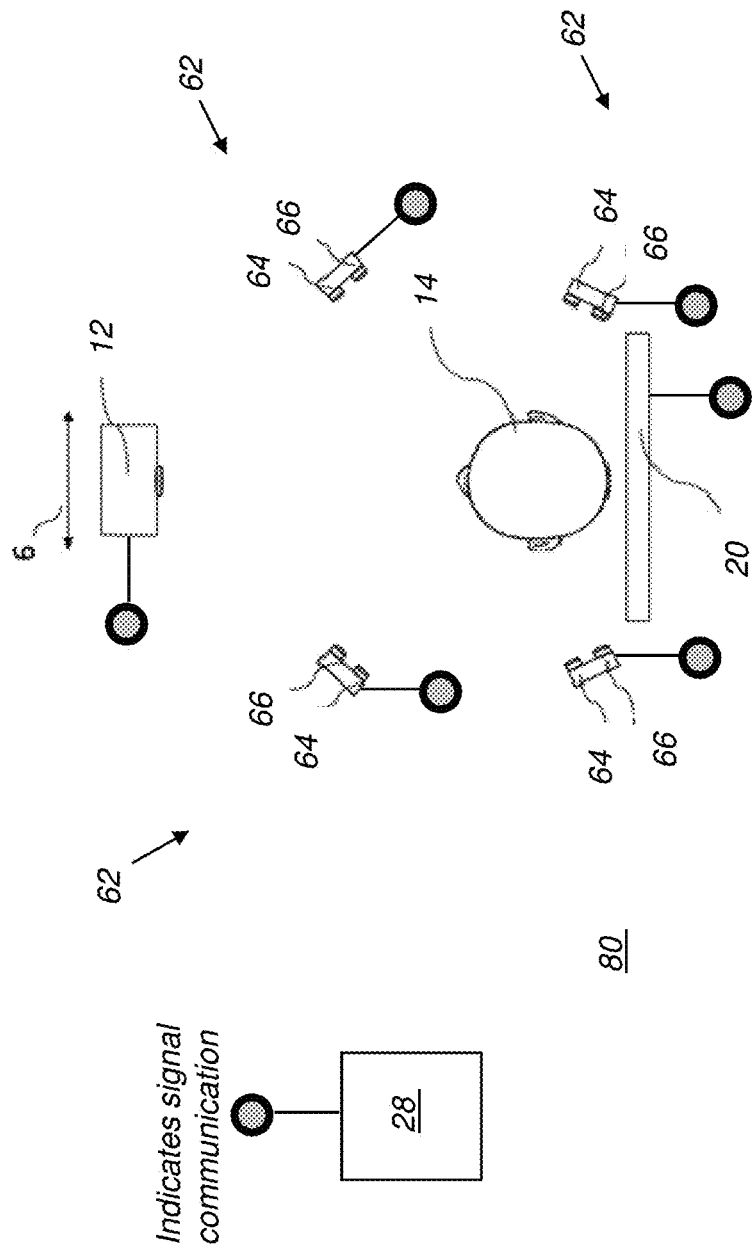
FIG. 3D is a schematic top view showing an imaging apparatus for chest tomosynthesis using multiple surface contour acquisition devices placed outside of the imaging system.

FIG. 3D is a schematic top view showing an imaging apparatus 80 for chest tomosynthesis having multiple pairs of light projectors 64 and sensors 66 as scanner 62, external to the x-ray acquisition components.

Figure 3E:
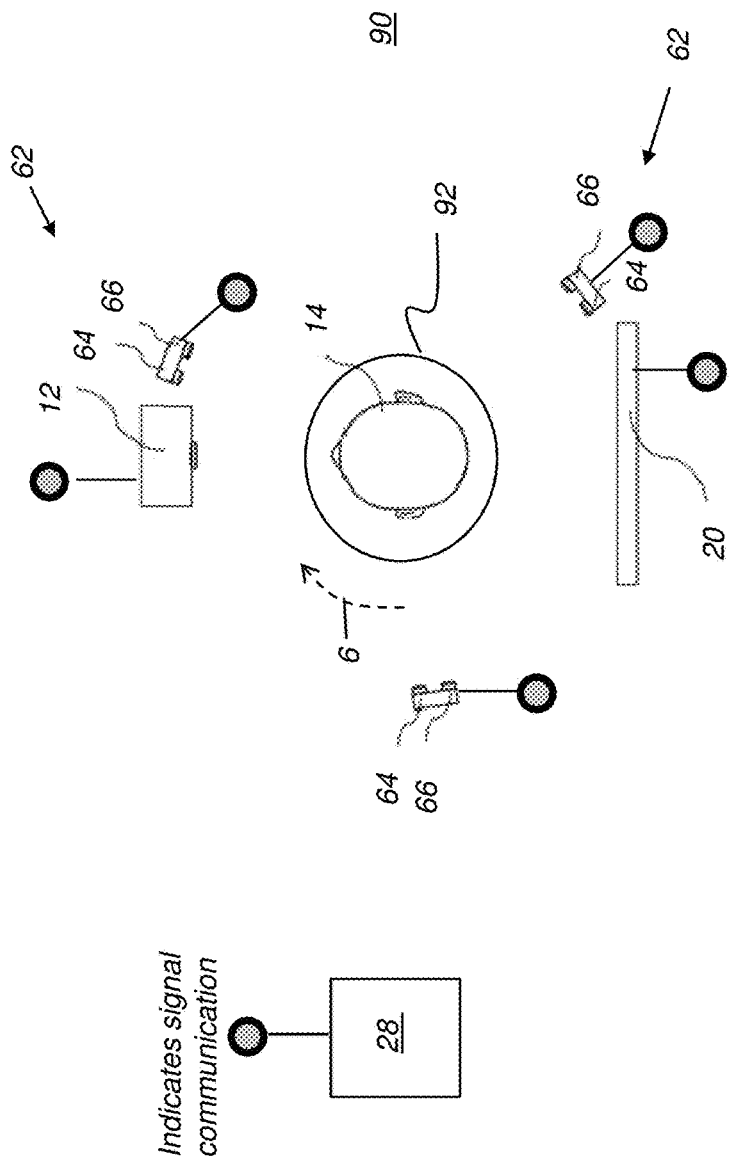
FIG. 3E is a schematic top view diagram that shows a computed tomography (CT) imaging apparatus with a rotating subject on a support and with a stationary X-ray source X-ray detector and multiple surface contour acquisition devices.

FIG. 3E is a schematic top view diagram that shows a computed tomography (CT) imaging apparatus 90 with stationary source 12 and detector 20 and rotating subject 14 on a support 92 that provides a transport apparatus for patient rotation. Stationary scanners 62 for surface contour acquisition are positioned outside the x-ray scanner hardware.

FIG. 3F is a schematic view diagram that shows an extremity X-ray imaging apparatus for volume imaging, having an x-ray source 12 and detector 20 configured to orbit about subject 14, and having multiple surface contour acquisition devices, scanners 62 that can move independently on rails 8 during projection data acquisition.

Figure 3G:
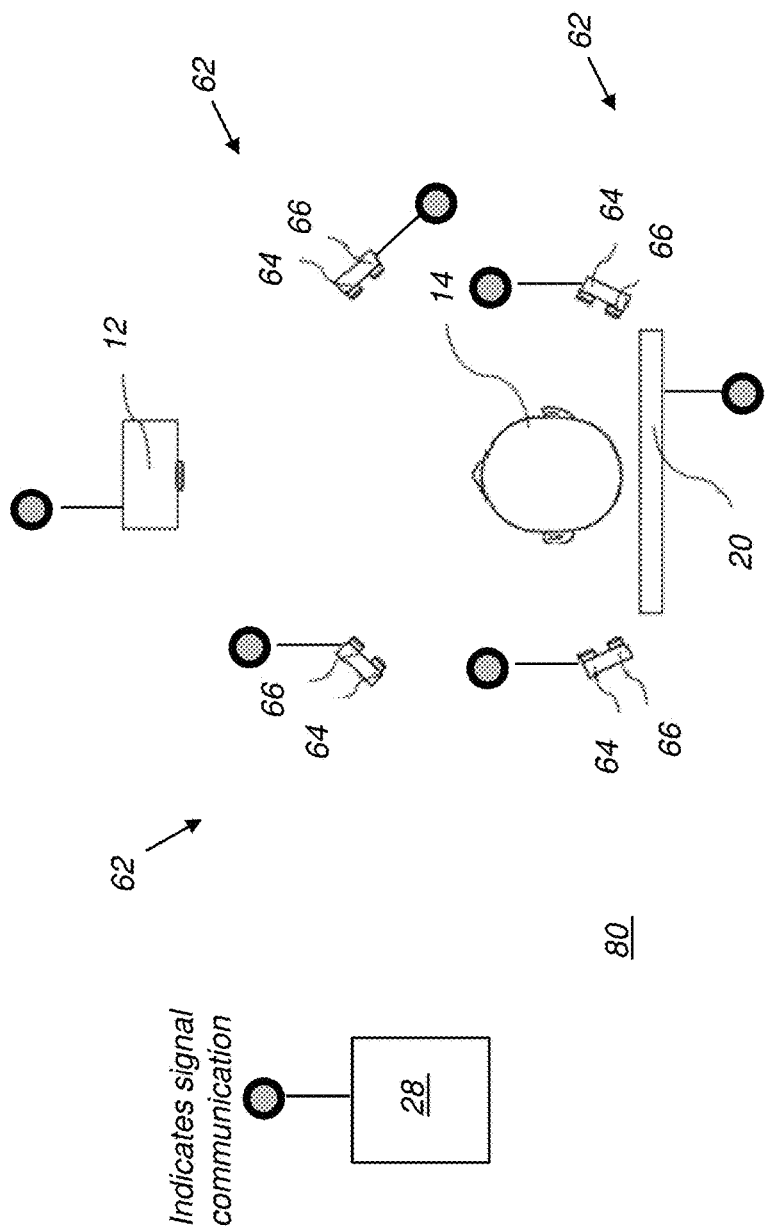
FIG. 3G is a schematic top view showing an imaging apparatus for chest radiographic imaging using multiple surface contour acquisition devices positioned outside of the imaging system.

FIG. 3G is a schematic top view showing imaging apparatus 80 for chest radiographic imaging using multiple scanners 62 to provide multiple surface contour acquisition devices positioned outside of the imaging system.

The moving trajectories of the X-ray sources and X-ray detectors can be, for example, helix (e.g., MDCT), full circle (e.g., dental CBCT CT), incomplete circle (e.g., extremity CBCT), line, sinusoidal, and stationary (e.g., low-cost CT), or other suitable movement pattern.

Motion Artifact Reduction

To help reduce motion artifacts in X-ray images, the Applicants propose a motion artifact reduction (MAR) system and method. The motion artifact reduction (MAR) system includes: a surface acquisition or characterization system for generating 3D surface models of a patient; an X-ray volume imaging apparatus for acquiring X-ray projection data of a patient; a controller to synchronize the surface acquisition system and the X-ray imaging apparatus; and a control logic processor (for example, a processor or other computing device that executes a motion reduction algorithm, or the like) that uses the X-ray projection data and 3D surface models to reconstruct a 3D volume, wherein the reconstructed volume has reduced patient motion artifacts.

In some cases, patient motion from a given position can be significant and may not be correctable. This can occur, for example, when the patient coughs or makes some other sudden or irregular movement. In the later reconstruction phase, the control logic processor 28 or controller 38 can suspend acquisition by the X-ray imaging system until the patient can recover the previous position.

The control logic can also analyze the acquired 3D surface image of the patient in real time and perform motion gating acquisition (also termed respiration gating) based on this analysis. With motion gating, surface contour acquisition can be associated with x-ray projection image acquisition and may even be used to momentarily prevent or defer acquisition. Using the controller to monitor and coordinate image acquisition, at least one 3D surface model of the patient can be obtained for each 2D X-ray projection. The acquired 3D surface model can be used for motion reduction in the reconstruction phase.

The schematic diagram of FIG. 4 shows one problem that is addressed for reducing motion artifacts according to an embodiment of the present disclosure. Normal patient breathing or other regular movement pattern can effectively change the position of a voxel V1 of subject 14 relative to x-ray source 12 and detector 20. At exhalation, the position of voxel V1 appears as shown. At full inhalation, the position shifts to voxel V1'. Without some type of motion compensation for each projection image, the wrong voxel position can be updated in 3D reconstruction.

Embodiments of the present disclosure provide motion compensation methods that characterize patient motion using imaging techniques such as surface contour imaging. A 3D surface model is generated from the acquired surface contour images and is used to generate transformation parameters that modify the volume reconstruction that is formed. Synchronization of the timing of surface contour imaging data capture with each acquired 2D x-ray projection image allows the correct voxel to be updated where movement has been detected. Because 3D surface contour imaging can be executed at high speeds, it is possible to generate a separate 3D surface contour image corresponding to each projection image 20 (FIG. 1). Alternately, contour image data can be continuously updated, so that each projection image 20 corresponds to an updated 3D surface model.

There are two classic computational approaches used for 3D volume image reconstruction: (i) an analytic approach that offers a direct mathematical solution to the reconstruction process; and (ii) an iterative approach that models the imaging process and uses a process of successive approximation to reduce error according to a cost function or other type of objective function. Each of these approaches has inherent strengths and weaknesses for generating accurate 3D reconstructions.

Figure 5:
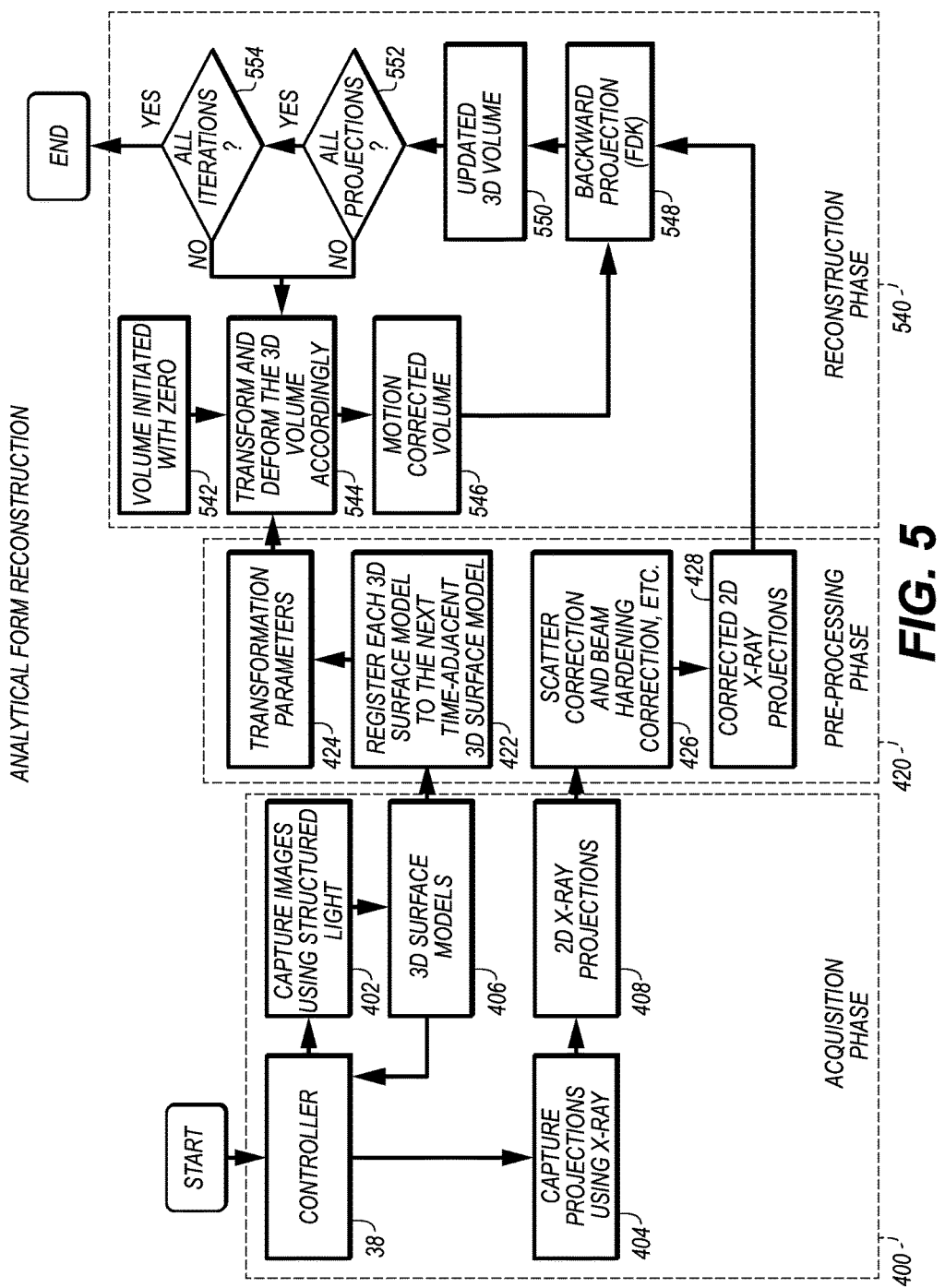
FIG. 5 is a logic flow diagram illustrating a method using the analytical form reconstruction algorithm for 3D motion reduction.
Figure 6:
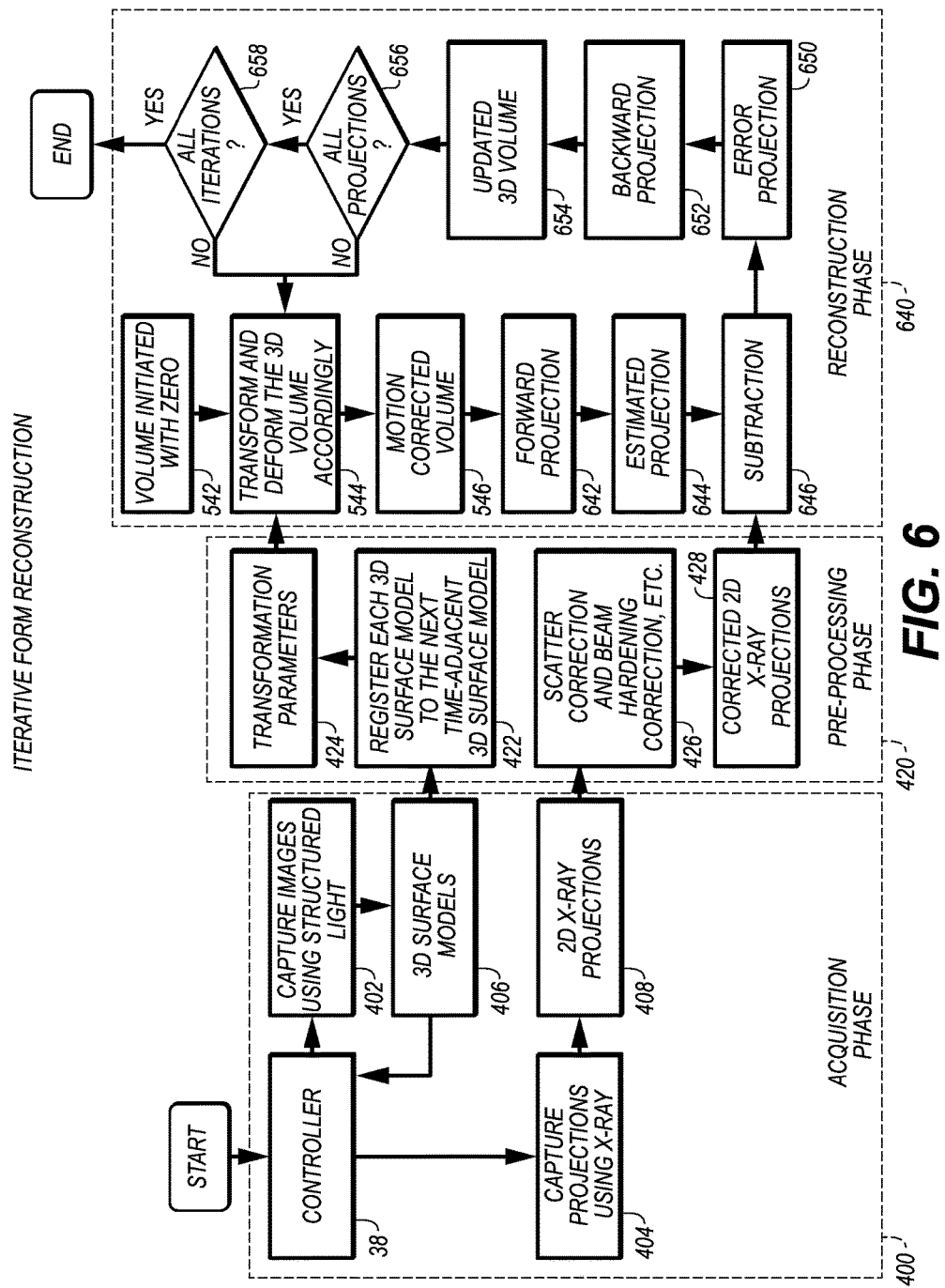
FIG. 6 is a logic flow diagram illustrating a method using the iterative form reconstruction algorithm for 3D motion reduction.

The logic flow diagram of FIG. 5 shows an overall process for integrating motion correction into volume data generation processing when using analytical techniques for volume reconstruction. Alternately, the logic flow diagram of FIG. 6 shows processing when using iterative reconstruction approaches for volume reconstruction. In both FIGS. 5 and 6, three phases are shown. The first two phases, an acquisition phase 400 and a pre-processing phase 420 are common whether analytic or iterative reconstruction is used. Following these phases, a reconstruction phase 540 executes for analytical reconstruction techniques or, alternately, a reconstruction phase 640 executes for iterative reconstruction techniques.

Referring to FIGS. 5 and 6, in acquisition phase 400, controller 38 captures 3D surface contour images, such as structured light images from scanner 62, in a scanning step 402. Controller 38 also coordinates acquisition of x-ray projection images 408 from detector 20 in a projection image capture step 404. Controller 38 and its associated control logic processor 28 use the captured 3D surface contour images to generate one or more 3D surface models in a surface model generation step 406 in order to characterize the surface contour at successive times, for synchronization of projection image data with surface contour information.

In pre-processing phase 420 of FIGS. 5 and 6, the 3D surface models generated from contour imaging can be registered to previously acquired surface models in a registration step 422. A set of transformation parameters 424 is generated for the surface contour data, based on changes detected in surface position from registration step 422. This transformation information uses the sequence of contour images and is generated based on changes between adjacent contour images and time-adjacent 3D surface models. 3D surface registration can provide and use rigid-object registration algorithms, such as to account for patient body translation and rotation, for example. In addition, 3D surface registration can provide and use deformable registration algorithms, such as to account for chest movement due to breathing and joint movement.

A correction step 426 then serves to provide a set of corrected 2D x-ray projections 428 for reconstruction. Correction step 426 can provide a number of functions, including scatter correction, lag correction to compensate for residual signal energy retained by the detector from previous images, beam hardening correction, and metal reduction, for example.

Continuing with the FIG. 5 process, a reconstruction phase 540 using analytic computation then integrates surface contour imaging and x-ray projection imaging results for generating and updating a 3D volume 550 with motion compensation. Transformation parameters 424 from pre-processing phase 420 are input to a transformation step 544. Step 544 takes an initialized volume from an initiation step 542 and applies transformation parameters 424 from pre-processing phase 420 to generate a motion-corrected volume 546. The corrected 2D x-ray projections 428 and the motion-corrected volume data then go to a reconstruction step 548. Reconstruction step 548 executes backward projection, using the FDK (Feldkamp-Davis-Kress) algorithm as in the example shown in FIG. 5 or other suitable analytical reconstruction technique, to update the motion corrected volume 546. A decision step 552 determines whether or not all projection images have been processed. A decision step 554 then determines whether or not all iterations for reconstruction have been performed. At the completion of this processing, the reconstructed 3D volume is corrected for motion detected from surface contour imaging.

The FIG. 6 process uses iterative processing in its reconstruction phase 640. Transformation parameters 424 from pre-processing phase 420 are input to transformation step 544. Step 544 takes an initialized volume from initiation step 542 and applies transformation parameters 424 to generate motion-corrected volume 546. The iterative process then begins with a forward projection step 642 that performs forward projection through the 3D volume to yield an estimated 2D projection image 644. A subtraction step 646 then computes a difference between the estimated 2D X-ray projections and the corrected 2D X-ray projection to yield an error projection 650. The error projection 650 is used in a backward projection step 652 to generate an updated 3D volume 654 using a SART (simultaneous algebraic reconstruction technique) algorithm, statistical reconstruction algorithm, total variation reconstruction algorithm, or iterative FDK algorithm, for example. A decision step 656 determines whether or not all projection images have been processed. A decision step 658 then determines whether or not all iterations for reconstruction have been performed. Iterative processing incrementally updates the 3D volume until a predetermined number of cycles have been executed or until an error value between estimated and corrected projections is below a given threshold. At the completion of this processing, the reconstructed 3D volume is corrected for motion detected from surface contour imaging.

By way of example, images illustrating motion artifacts can be found in Boas, F. Edward, and Dominik Fleischmann. "CT artifacts: causes and reduction techniques." *Imaging in*

Figures 7A, 7B:
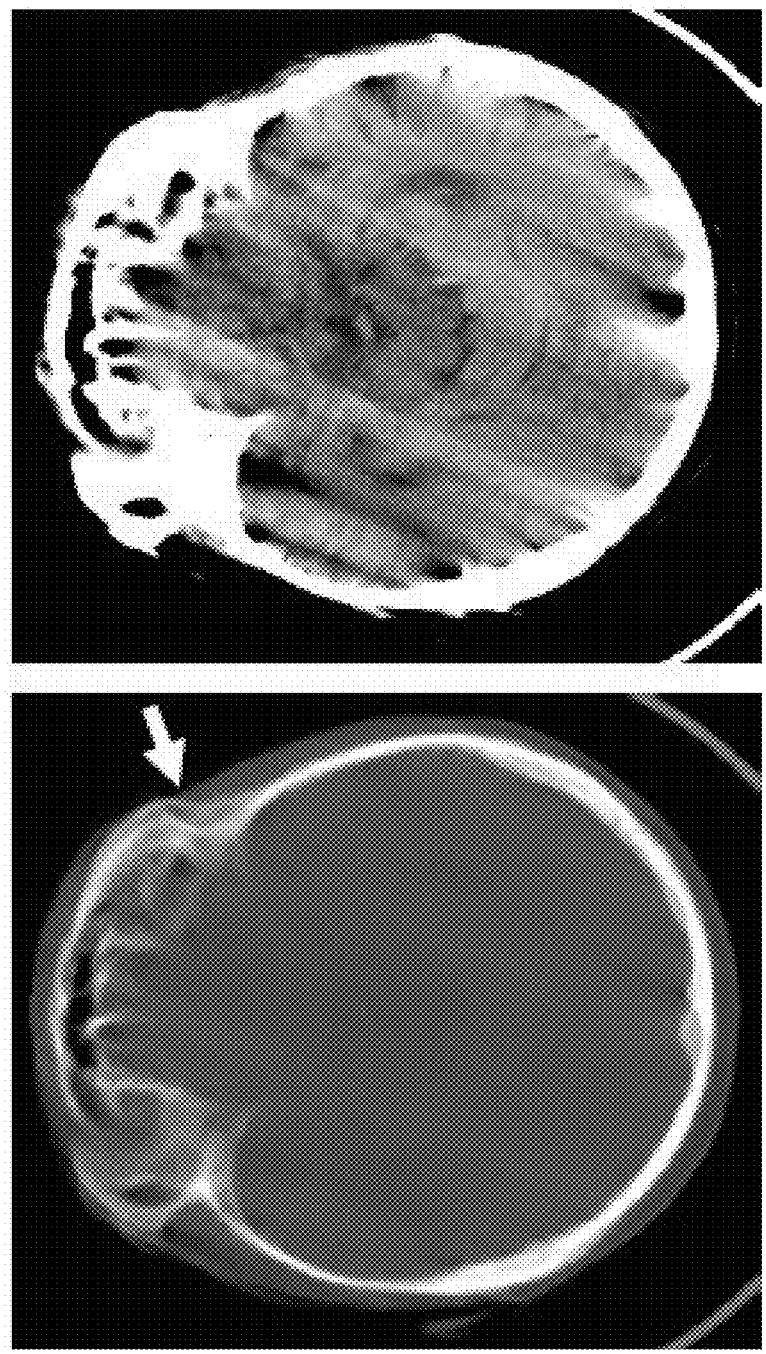
FIG. 7A shows a computed tomography image illustrating blurring and double images caused by motion.
FIG. 7B shows a computed tomography image illustrating long range streaks caused by motion.

*Medicine* 4.2 (2012): 229-240.', incorporated herein in its entirety. Motion artifacts can include blurring and double images, as shown in FIG. 7A and streaks across the image as shown in FIG. 7B.

Figure 8:
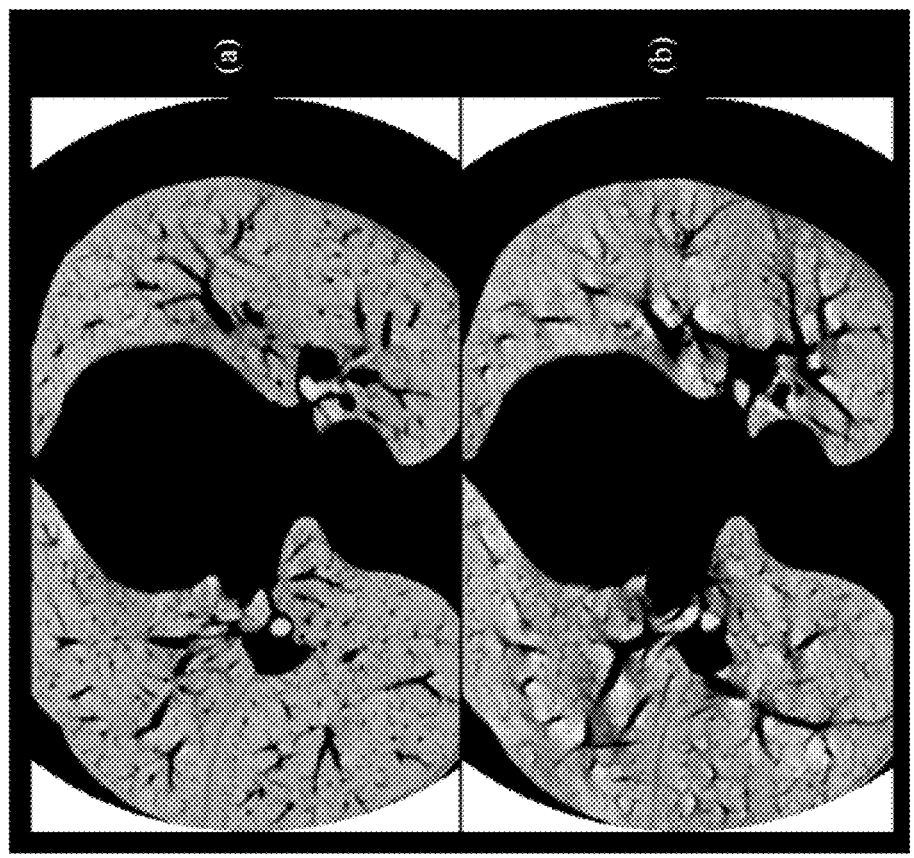
FIG. 8 shows a respiratory motion artifact for a chest scan.

Reference is made to Hsieh, Jiang. "Computed tomography: principles, design, artifacts, and recent advances." Bellingham, Wash.: SPIE, 2009, pages 258-269 of Chapter 7. This reference describes a respiratory motion artifact, as best illustrated in FIG. 8, wherein (a) is a chest scan relatively free of respiratory motion and (b), for the same patient, shows artifacts due to being scanned during breathing.

Accordingly, Applicants have disclosed a system for constructing a 3D volume of an object, comprising: a surface acquisition system for acquiring 3D surface images of the object; an X-ray imaging system for acquiring a plurality of X-ray projection images of the object; a controller to synchronize control the surface acquisition system and the X-ray imaging system to acquire the 3D surface images and X-ray projection images; and a processor to construct a 3D volume using the acquired 3D surface images and X-ray projection images.

Accordingly, Applicants have disclosed a method for reconstructing a 3D volume, comprising: providing a synchronized system comprised of a surface acquisition system and a X-ray imaging system; using the synchronized system, acquiring a plurality of surface images and a plurality of X-ray projection images of a patient; generating a plurality of 3D surface models of the patient using the plurality of surface images; and reconstructing the 3D volume using the plurality of X-ray projection images and the plurality of 3D surface models. In one embodiment, the step of reconstructing the 3D volume employs an analytical form reconstruction algorithm. In another embodiment, the step of reconstructing the 3D volume employs an iterative form reconstruction algorithm.

It can be appreciated that other processing sequences can alternately be executed using the combined contour image and projection image data to compensate for patient motion as described herein.

Consistent with one embodiment, the present invention utilizes a computer program with stored instructions that control system functions for image acquisition and image data processing for image data that is stored and accessed from an electronic memory. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A system for reconstructing a 3D volume, comprising:
   a surface acquisition apparatus comprising a light source, a scanner, and an image sensor to generate a 3D surface contour characterization of a patient;
   an X-ray imaging system for acquiring 2D X-ray projection data of the patient from a plurality of angular positions;
   a controller programmed with instructions to synchronize the 3D surface contour characterization from the surface acquisition apparatus with the acquired 2D X-ray projection data; and
   a processor comprising a motion reduction algorithm that uses the acquired 2D X-ray projection data and the generated 3D surface contour characterization to reconstruct a 3D volume, and a motion correction reconstruction algorithm applied to the reconstructed 3D volume to generate a motion corrected reconstructed 3D volume.

2. The system of claim 1, wherein the surface acquisition apparatus further comprises:
one or multiple light sources configured to project a predetermined light pattern onto the patient;
one or multiple optical sensors configured to capture a plurality of 2D digital images of the light pattern on the patient; and
a surface contour reconstruction program that reconstructs the 3D surface model of the patient using the captured 2D digital images.

3. The system of claim 2 wherein the light sources and the optical sensors are mounted to a rotational gantry of the X-ray imaging system.

4. The system of claim 2 wherein the light sources and the optical sensors are affixed to a bore of the X-ray imaging system or placed outside of the X-ray imaging system.

5. The system of claim 1, wherein the controller monitors the patient motion, and wherein the controller stops acquisition by the x-ray imaging system according to the patient motion.

6. The system of claim 5 wherein the controller performs motion gating.

7. The system of claim 1, wherein the scanner includes a projector adapted to direct, using the light source, a structured light pattern toward the patient, which are recorded by the image sensor.

8. The system of claim 1, wherein the motion reduction algorithm further comprises: an X-ray projection correction process that yields corrected 2D X-ray projections; a 3D surface registration algorithm that registers each 3D surface model to the next time-adjacent 3D surface model and yields the transformation parameters; and an analytical form or an iterative form motion correction reconstruction algorithm.

9. A system for reconstructing a 3D volume, comprising:
a surface acquisition apparatus comprising a light source, a scanner, and an image sensor to generate a 3D surface contour characterization of a patient;
an X-ray imaging system for acquiring 2D X-ray projection data of the patient from a plurality of angular positions;
a controller programmed with instructions to synchronize the 3D surface contour characterization from the surface acquisition apparatus with the acquired 2D X-ray projection data; and
a processor comprising a motion reduction algorithm that uses the acquired 2D X-ray projection data and the generated 3D surface contour characterization to reconstruct a 3D volume, and a motion correction reconstruction algorithm applied to the reconstructed 3D volume to generate a motion corrected reconstructed 3D volume, wherein the surface acquisition apparatus acquires at least one 3D surface model for each 2D X-ray projection image.

10. A system for reconstructing a 3D volume, comprising:
a surface acquisition system comprising a light source and an image sensor for characterizing the surface contour of a patient;
an X-ray imaging system for acquiring X-ray projection data of the patient from a plurality of angular positions, the X-ray imaging system comprising:
one or multiple X-ray sources to controllably emit X-rays in response to incident electrons; and
one or multiple X-ray detectors including a plurality of rows of X-ray sensors able to detect X-rays that are emitted from the X-ray sources and that have traversed the patient;
a controller programmed with instructions to synchronize the 3D surface contour characterization from the surface acquisition system with the acquired X-ray projection data; and
a processor that executes a motion reduction method that uses the acquired X-ray projection data and the generated 3D surface contour characterization to reconstruct a 3D volume, wherein the motion reduction method further comprises:
an X-ray projection correction process that yields corrected 2D X-ray projections;
a 3D surface registration algorithm that registers each 3D surface model to the next time-adjacent 3D surface model and yields the transformation parameters; and
an analytical form reconstruction algorithm or an iterative form reconstruction algorithm.

11. The system of claim 10, wherein moving trajectories of the X-ray sources and X-ray detectors can be helical, full circle, incomplete circle, line, sinusoidal, or stationary.

12. The system of claim 10 further comprising an algorithm that adjusts the relative location of the patient to the X-ray source and to the detector to compensate for patient movement.

13. The system of claim 10, wherein the X-ray projection correction process provides at least one of scatter correction, lag correction, beam hardening correction, and metal reduction.

14. The system of claim 10, wherein the 3D surface registration algorithm provides rigid-object registration algorithms and deformable registration algorithms.

15. The system of claim 10, wherein the analytical form reconstruction algorithm further comprises:
initializing the 3D volume; and
for each projection:
(i) transforming the 3D volume based on pre-determined transformation parameters to correct for the patient motion; and
(ii) updating the corrected 2D X-ray projection to the 3D volume using an analytical reconstruction algorithm.

16. The system of claim 10, wherein the iterative form reconstruction algorithm initiates the 3D volume for each projection, transforms the 3D volume based on pre-determined transformation parameters to correct for the patient motion performs forward projection through the 3D volume to yield estimated 2D X-ray projection, subtracts the estimated 2D X-ray projections from the corrected 2D X-ray projection to yield error projection, updates the error projection to the 3D volume, and repeatedly updates the 3D volume.

17. The system of claim 16 wherein the algorithm updates the error projection using one of a simultaneous algebraic reconstruction technique algorithm, a statistical reconstruction algorithm, a total variation reconstruction algorithm, or an iterative FDK algorithm.

18. A method for reconstructing a 3D volume, the method executed at least in part on a computer system, comprising:
providing a synchronized system comprising a surface acquisition apparatus and an X-ray imaging system;
using the synchronized system, acquiring a plurality of surface images and a plurality of X-ray projection images of a patient;

generating a plurality of 3D surface models of the patient using the plurality of surface images;
reconstructing the 3D volume using the plurality of X-ray projection images;
using the plurality of generated 3D surface models, applying a motion artifact reduction reconstruction algorithm to the reconstructed 3D volume to generate a plurality of motion corrected X-ray projection images;
using the plurality of motion corrected X-ray projection images, reconstructing a motion corrected 3D volume; and
displaying, storing, or transmitting at least a portion of the motion corrected reconstructed 3D volume.

19. The method of claim 18, wherein reconstructing the 3D volume includes applying either (a) an iterative form reconstruction algorithm or (b) an analytical form reconstruction algorithm.

20. The method of claim 18 wherein acquiring the plurality of surface images comprises using one or more contour imaging apparatus mounted on rails.

* * * * *